United States Patent
Lai et al.

(10) Patent No.: US 8,157,378 B2
(45) Date of Patent: Apr. 17, 2012

(54) EYE ILLUMINATION APPARATUS AND METHOD

(75) Inventors: Ming Lai, Webster, NY (US); Barry T. Eagan, Spencerport, NY (US); Daozhi Wang, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 230 days.

(21) Appl. No.: 11/844,007

(22) Filed: Aug. 23, 2007

(65) Prior Publication Data

US 2009/0051873 A1 Feb. 26, 2009

(51) Int. Cl.
*A61B 3/10* (2006.01)
(52) U.S. Cl. ...................................................... 351/221
(58) Field of Classification Search .................. 351/205, 351/221, 200, 206, 209, 211, 212, 246; 606/4–5; 356/124
See application file for complete search history.

(56) References Cited

U.S. PATENT DOCUMENTS

| | | | |
|---|---|---|---|
| 5,286,964 A * | 2/1994 | Fountain | 250/201.2 |
| 6,000,799 A | 12/1999 | Van de Velde | |
| 6,264,328 B1 | 7/2001 | Williams et al. | |
| 6,270,221 B1 | 8/2001 | Liang et al. | |
| 6,271,914 B1 | 8/2001 | Frey et al. | |
| 6,271,915 B1 | 8/2001 | Frey et al. | |
| 6,460,997 B1 | 10/2002 | Frey et al. | |
| 6,497,483 B2 | 12/2002 | Frey et al. | |
| 6,598,975 B2 | 7/2003 | Liang et al. | |
| 6,908,196 B2 * | 6/2005 | Herekar et al. | 351/221 |
| 2003/0117581 A1 * | 6/2003 | Martino et al. | 351/221 |
| 2003/0189690 A1 * | 10/2003 | Mihashi et al. | 351/221 |
| 2003/0229339 A1 * | 12/2003 | Bille | 606/5 |
| 2004/0130677 A1 * | 7/2004 | Liang et al. | 351/205 |
| 2006/0077347 A1 | 4/2006 | Liang et al. | |
| 2007/0030450 A1 | 2/2007 | Liang et al. | |
| 2007/0195264 A1 * | 8/2007 | Lai | 351/177 |

FOREIGN PATENT DOCUMENTS

| | | |
|---|---|---|
| WO | WO 99/58047 A1 | 11/1999 |
| WO | WO 01/89374 A2 | 11/2001 |

OTHER PUBLICATIONS

Amnon Yariv, "Fundamental Gaussian Beam in a Lenslike Medium," Optical Electronics, (p. 32-34), (Jul. 1, 1985).
Gaussian Beam Propagation, "Transformation and Magnification by Simple Lenses," Melles Griot, (http://www.mellesgriot.com/products/optics/gb_2_3.htm).
Hecht, Geometrical Optics-Paraxial Theory, Optics, Second Edition, Lenses 5.2, pp. 137-139.
CVI Melles Griot, Gaussian Beam Optics, Gaussian Bean Propagation, www.cvimellesgriott.com, pp. 2.2-2.5.

(Continued)

*Primary Examiner* — Ricky Mack
*Assistant Examiner* — Mahidere Sahle
(74) *Attorney, Agent, or Firm* — Jeffrey B. Powers

(57) ABSTRACT

An ophthalmic apparatus adapted to project a waist of a beam of the light, such that a portion of the confocal region of the waist is projected onto the cornea. The source can be at least partially coherent and/or monochromatic. The source may be a laser or a laser diode. The beam can be a Gaussian beam, or a non-Gaussian beam. The apparatus can comprise a wavefront aberrometer, an axial eye length measuring apparatus or a refractometer.

30 Claims, 2 Drawing Sheets

OTHER PUBLICATIONS

Yariv, Optical Electronics, Third Edition, Gaussian Beams in a Homogeneous Medium, pp. 28-35.
Hecht, Geometrical Optics-Paraxial Theory, Optics, Second Edition, Lenses 5.2, pp. 137-139, 1987.
CVI Melles Griot, Gaussian Beam Optics, Gaussian Bean Propagation, www.cvimellesgriott.com, pp. 2.2-2.5, printed Jul. 2009.
Yariv, Optical Electronics, Third Edition, Gaussian Beams in a Homogeneous Medium, pp. 28-35, 1985.
Gaussian Beam Propogation, "Transformation and Magnification by Simple Lenses," Melles Griot, (http://www.mellesgriot.com/products/optics/gb_2_3.htm), printed Jun. 23, 2009.

\* cited by examiner

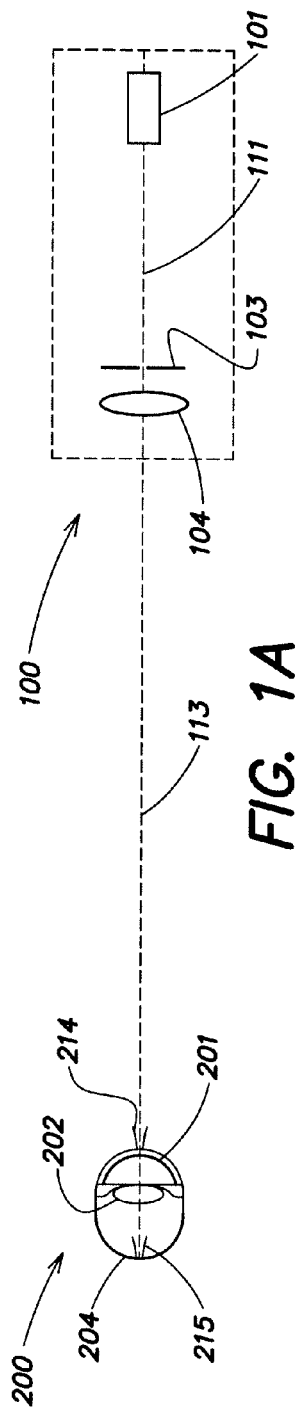
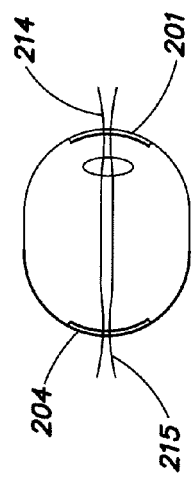
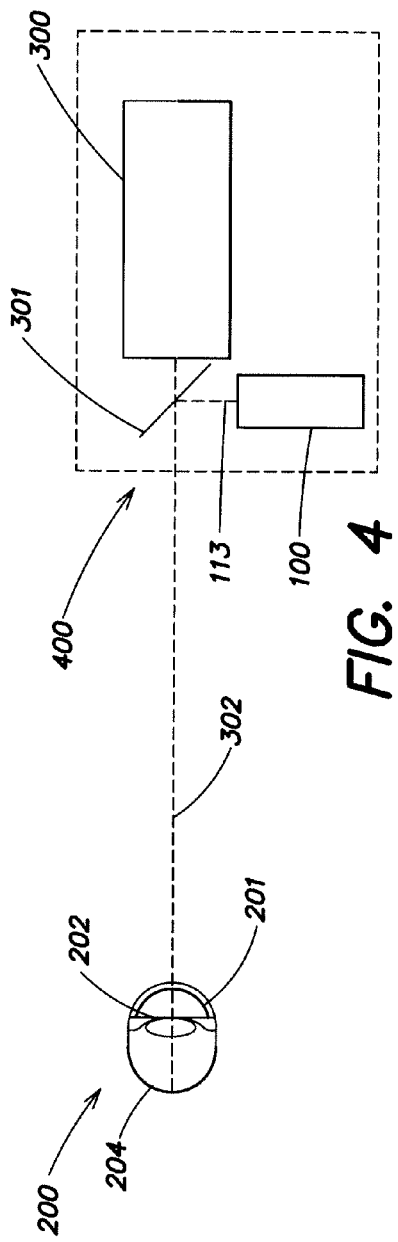
FIG. 1A
FIG. 1B
FIG. 4

EYE ILLUMINATION APPARATUS AND METHOD

FIELD OF INVENTION

The present invention relates to apparatus and methods for projecting beams of light into an eye.

BACKGROUND

The use of a Hartmann-Shack wavefront apparatus to determine ocular aberrations of subjects by measuring a wavefront emerging from an eye is known. To produce such an emerging wavefront, a laser beam is injected into the eye, and a spot of light formed on the retina is reflected from the retina to produce a wavefront emerging from the eye. The emerging wavefront is distorted by the eye's aberrations as it passes through the cornea, lens and other portions of the eye. Upon exiting the eye the wavefront is directed onto a sensor and the output of the sensor is provided to a calculator of aberrations.

A relatively small spot on the retina is desirable for producing a retinal reflection because it operates as a point source when producing an emerging wavefront. However, when a beam of light from a laser is injected into the eye, the size of the spot on the retina is affected by the refractive power of the cornea and the lens, as well as aberrations of the eye.

To achieve a suitably small spot on the retina, some conventional wavefront apparatus actively or statically compensate for myopia or hyperopia, and other aberrations. For example, in one apparatus, active compensation is achieved by movement of a focus corrector in a trombone stage that is located in front of subjects' eyes to adjust the location of the laser beam focus relative to each subject's retina.

In another conventional apparatus, a focusing lens is selected to have a long effective focal length to focus light onto subjects' corneas. In such static apparatus, a focusing lens, located at a fixed location, is arranged to project a geometrical focus onto subjects' corneas such that the impact of hyperopia and myopia is reduced and the impact of the aberrations of the subjects' eyes is also reduced. Since, the beam diverges after passing through a cornea (i.e., after passing through geometrical focus) the spot size at the retina is often larger than desired.

SUMMARY

Aspects of the present invention are directed to eye illumination apparatus for which a beam of light and an optic are selected such that a portion of the confocal region of a Gaussian beam is projected onto subjects' corneas. Another aspect of the invention is directed to projecting a non-Gaussian beam such that a diffraction-limited spot (i.e., a spot substantially in the shape of an Airy disk) is formed proximate the cornea and a portion of the confocal region and the spot is projected onto the cornea.

In some embodiments, a beam waist within the confocal region is projected onto the cornea. Aspects of the present apparatus rely on the subject's cornea and natural lens to transmit the beam such that a second beam waist is transferred into the vicinity of the subject's retina (i.e., such that a portion of the beam within a second confocal region is incident on the retina). As discussed in greater detail below, such apparatus have an advantage that, both, (1) a relatively small area of illumination occurs at the cornea, thereby reducing the impact of the corneal focal and aberration characteristics on the projected beam (It will be appreciated that, due to proximity of an eye's lens to its cornea, a small area of illumination also occurs at a subject's lens which similarly reduces the impact of the lens on the beam), and (2) a relatively small spot of illumination occurs on the retina, which operates substantially as a point source upon reflection from the retina. The size of the relatively small spot that occurs on the retina is substantially insensitive to a subject's myopia or hyperopia.

An aspect of the invention is directed to an ophthalmic apparatus adapted to project a beam of light onto a subject's cornea, the apparatus comprising a radiation source adapted to generate the light, and an optic. The apparatus is adapted to position the subject's cornea at a location proximate to a location where the radiation source and the optic project a waist of a beam of the light, such that a portion of the confocal region of the waist is projected onto the cornea.

In some embodiments, the apparatus is adapted to position the subject's cornea at the location where the radiation source and the optic project the waist.

In some embodiments, the optic constitutes a focal optical system. In other embodiments, the optic constitutes an afocal optical system.

The source may be at least partially coherent (i.e., the output of the source is at least partially coherent). The source may be monochromatic. In some embodiments, the source comprises a laser or a laser diode or a superluminescent diode.

The source may provide the light as a Gaussian output. The source may provide the light as a non-Gaussian output.

The apparatus may further comprise optics adapted to collimate the light to form the beam, before the waist is projected. An aperture may be included to select a size of the beam.

The beam projected onto the cornea may have a vergency of 5 milliradians or less. The vergency may be greater than 2 milliradians and less than 5 milliradians.

The apparatus may comprise a wavefront aberrometer, an axial eye length measuring apparatus or a refractometer.

Another aspect of the invention is directed to a method of illuminating a subject's eye, comprising projecting a beam waist of a beam of light such that a portion of the confocal region of the waist is projected onto the subject's cornea.

In some embodiments, the step of projecting comprises projecting the beam waist onto the cornea. The light may be monochromatic.

The method may further comprise a step of generating the beam from an output of a laser or a laser diode or a superluminescent diode.

The beam may be a Gaussian beam output of a laser.

The method may further comprise a step of generating a non-Gaussian output of the light, prior to the step of projecting. The method may further comprise a step of collimating the non-Gaussian output to form the beam, prior to the step of projecting. The method may further comprise a step of selecting a size of the beam using an aperture, prior to the step of projecting.

The projected beam may have a vergency of 5 milliradians or less. The step of projecting may comprise transferring another beam waist of a source (e.g., a laser having a $TM_{00}$ mode output).

The term "beam waist" as used herein refers to a location along a beam where the beam radius is a local minimum and where the wavefront of the beam is planar over a substantial length (i.e., a confocal length). The term "working distance" as used herein means the distance between the surface of the optic that is closest to a subject's eye and the target plane (i.e., the position where an apparatus is designed to hold the front surface of a subject's cornea).

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 1A is a schematic illustration of an example of an embodiment of an ophthalmic apparatus according to aspects of the present invention in which the apparatus is projecting light onto a subject's eye;

FIG. 1B is an expanded view of the eye of FIG. 1A;

FIG. 4 is a schematic illustration of an example of an aberrometer according to aspects of the present invention including a beam projection system and receive optics suitable for use in determining wavefront aberrations.

DETAILED DESCRIPTION

Figure 2:
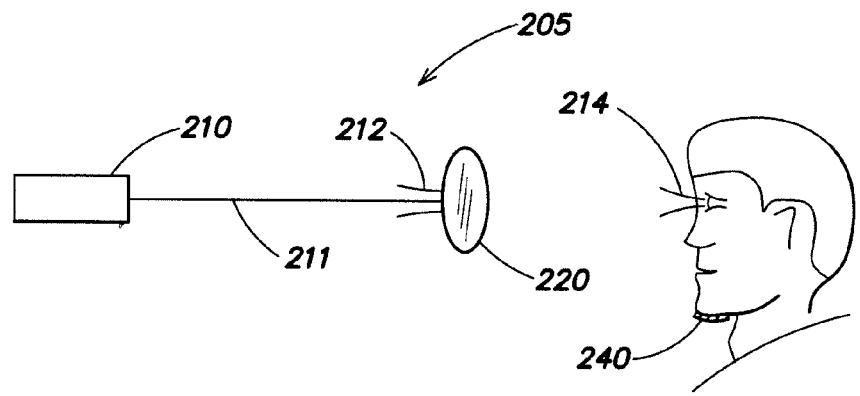
FIG. 2 illustrates one example a suitable projection apparatus.

FIG. 1A is a schematic illustration of an example of an embodiment of an ophthalmic apparatus 100 projecting light onto a subject's eye 200 according to aspects of the present invention. The apparatus includes a radiation source 101 adapted to generate light 111, and an optic 104. The radiation source and the optic are configured and arranged to project a beam waist 214 onto a subject's cornea 201.

The ophthalmic apparatus illustrated in FIG. 1 may be, for example, a beam injection system for a wavefront aberrometer. An embodiment of an aberrometer according to aspects of the present invention is discussed below with reference to FIG. 4. However, illumination apparatus according to aspects of the present invention may be used in any suitable ophthalmic apparatus. Another example of a device comprising an illumination apparatus according to aspects of the invention is an axial length measurement apparatus as discussed below with reference to FIG. 5. Yet a further example is a refractometer (not shown).

Radiation source 101 may be any suitable source for generating light to be projected in a beam. For example, a source may comprise a laser source. A laser may be suitable due to its ability to provide a Gaussian beam output of adequate intensity. In some embodiments, the radiation source is selected to be a laser diode due to the compact size, reliability and low cost of such devices; however, laser diodes are typically multimode (i.e., non-Gaussian) and may require processing (e.g., truncation by an aperture and/or lensing) to provide a beam which provides a beam waist similar to a Gaussian beam. The radiation source may comprise another suitable coherent or partially coherent source of radiation (e.g., a superluminescent diode (SLD)). In some embodiments, the light projected onto the eye has a power in the range of 0.1 to 10 mW at a wavelength of 400 to 1000 nm.

In some embodiments, the source may be coherent and/or monochromatic; however a source need not be coherent or monochromatic. At present, sources capable of providing light for producing beams of suitable intensity are at least partially coherent and monochromatic; however, any currently known or later developed source capable of providing light sufficient to generate a beam (with a beam waist) of suitable intensity may be used.

Optic 104 may comprise a lens, a diffractive optical element, holographic element or any other suitable optical element or combination of optical elements to project a beam waist of appropriate size onto (or proximate) a cornea. In some embodiments, the focal length of the optical element is approximately equal to the working distance of the apparatus. For example, the working distance of apparatus 100 may be 100 to 300 mm.

In some embodiments, light output 111 of light source 101 is a Gaussian beam having a first beam waist (not shown). Accordingly the beam propagates according to Gaussian optics, and an optic 104 transfers a beam waist to the cornea provided that the beam vergence (after the beam passes through the optic) is suitably small. In such embodiments, a waist 214 is thereby projected onto a cornea 201.

In other embodiments, light output 111 is other than a Gaussian beam (e.g., a multiple order beam output from a laser diode). In such embodiments, output 111 may be collimated using suitable optics (not shown) and an aperture 103 (e.g., a pinhole) may be included to select a size of the beam (e.g., a diameter) transmitted by the lens. Due to diffraction, the smaller the aperture is, the larger the beam size at waist 214 (i.e., at the subject's cornea). In embodiments including an aperture, the aperture is located suitably close to optic 104 to determine the vergence angle of the beam after passing through the optic.

It will be appreciated that, in such embodiments, due to wave nature of light, by making the beam diameter suitably small (e.g. a 1 mm diameter aperture used with an optic 104 having a 300 mm focal distance), the beam projected onto the cornea will be diffraction-limited (i.e., the beam will form a beam waist having a spot in the shape of an Airy disk) and will propagate similar to a Gaussian beam (i.e., the beam is similar to a propagating Gaussian beam). Such a beam will have no clear focal plane; rather, the beam will have planar wavefronts over a substantial length (i.e., the beam has a confocal region) and, in an eye, will be capable of forming a second beam waist (with a corresponding confocal region) in the vicinity of the retina.

An aperture may be used in a system in which a Gaussian beam is provided by the source. For example, an aperture may be used to control the beam size at a transferred waist of such a beam.

As mentioned above, the apparatus 100 is adapted to position a subject's cornea. Typically, the instrument is provided with a subject-positioning apparatus suitable for maintaining the subject's head such that the subject's cornea is positioned with the beam waist of the source projected proximate the subject's cornea by optic 104. A suitable positioning apparatus may include a forehead rest and/or a chin rest.

The subject's cornea 201 and lens operate to provide focal power to transfer a second beam waist 215 in the vicinity of the subject's retina 204.

In some embodiments, it is advantageous to have a relatively small area of illumination on the cornea: 1) to reduce the impact of the aberrations of a subject's cornea and lens, and 2) to reduce the size of the specular reflections generated by the cornea and lens, which typically makes it easier to control or avoid specular reflections when collecting the light exiting from the eye on a sensor.

Additionally it will be appreciated that, for a Gaussian beam such as beam 113, the spot size varies relatively little on the near side of the beam waist (i.e., between the beam waist and the light source) and on the far side of the beam waist. Accordingly, an advantage of embodiments of the present invention is that, if the second beam waist does not coincide with the retina (e.g., due to a subject's myopia or hyperopia)

the spot size on the retina will not be much larger than the beam waist. For example, if an embodiment is designed such that, for an emmotropic eye having a given eye length, a second beam waist will be projected proximate the retina, the apparatus will be relatively insensitive to variations in location of the second beam waist relative to the retina that result from variations in subjects' eye lengths or subjects' hyperopia or myopia.

FIG. 1B is an expanded view of the eye of FIG. 1A illustrating a first beam waist 214 projected onto cornea 201 and a second beam waist 215 projected into the vicinity of the retina 204. The scale of the beam is greatly enlarged relative to the eye to facilitate viewing.

In summary, apparatus according to aspects of the present invention provide advantages of a small area of illumination on subjects' retinas due to (1) a relatively small area of illumination at the cornea (i.e., an area determined in part by a first beam waist) thereby reducing the impact of corneal aberrations and variations among subjects' focusing powers; and (2) the presence of a second beam waist in proximity of the retina. Accordingly, the apparatus provides a relatively high quality point source upon reflection of the beam from the retina for a range of defocus (e.g., defocus caused by a subject's myopia or hyperopia) and a range of subjects' eye lengths.

The following discussion describes a design technique for designing examples of embodiments according to aspects of the present invention. The design technique illustrates one example of a method of design and is not intended to limit the scope of any claimed apparatus or method of using an apparatus.

According to an example implementation of the technique, it is assumed that a nominal eye is emmotropic and has a length from the corneal front surface to the retinal front surface of 22 mm, and the combined focal power of the cornea and lens of the nominal eye is 60 diopters. Further according to the example implementation of the technique, a confocal parameter $L_0$ of the laser beam (i.e., the axial distance over which the beam diameter remains within a factor of $\sqrt{2}$ (approximately a factor of 1.4) of the beam waist) is selected to be equal to the distance between the focal points that will occur if the nominal focal power is increased by 12 diopters (i.e., 12 diopters of myopia) or decreased by 12 diopters (i.e., 12 diopters of hyperopia). The design parameter of +/−12 diopters relative to nominal is selected by way of example and any suitable variation in optical power may be selected. Said distance is equal to about 8 mm, in the above embodiment (i.e., +/−4 mm from nominal). Accordingly, by choosing a beam having a confocal distance of 8 mm, it will be ensured that the beam diameter will be no greater than about 1.4 times the beam waist diameter, provided that a subject's eye has focal power of between 48 diopters and 72 diopters.

Confocal parameter $L_0$ (defining a confocal region of the beam) and beam waist $2W_0$ are related as shown in Equation 1.

$$L_0 = 2\pi n\, W_0^2/\lambda \qquad \text{Equation 1}$$

Accordingly, assuming a probe beam wavelength λ of 800 nanometers and an average eye index of refraction n of 1.33 for the above example, to achieve a confocal distance of 8 mm, the beam waist ($2W_0$) is selected to be 56 microns. As a result, the size of the defocused beam spot size on the retina that would result due to a change of +12 diopters to −12 diopters from a nominal focal power of 60 diopters will be in the range 56 microns ($2W_0$) to 78 microns ($1.4 \ast 2W_0$).

Equation 2, below, can be used to calculate the beam size on the cornea that a beam would need to provide a beam waist on the retina equal to 56 microns.

$$2W = 2W_0 \sqrt{(1+(z/z_0)^2)} \qquad \text{Equation 2}$$

where z is a distance from the location of beam waist $2W_0$; and 2W is the beam size at location z.

It follows from Equation 2 that, at a surface 22 mm from the retinal beam waist location (i.e., at a location on a cornea located at a distance equal to the nominal eye length in front of the retina), the beam diameter of the propagating Gaussian beam would be 300 microns (um). That is, a probe beam having a waist of 300 micron at the location where the cornea will be located by the apparatus will provide a second beam having a 56 micron (um) diameter at the retina of a nominal eye.

Although a nominal eye length of 22 mm, a nominal optical power of the eye of 60 diopters, a wavelength of 800 nm and a working distance of 300 mm were used in the example above, any suitable design parameters may be used.

Any suitable projecting apparatus capable of projecting a beam waist of 300 microns onto a subject's cornea could be used in the above example to achieve an injection system as described above. Examples of suitable projection apparatus are given below.

In some embodiments, the first beam waist (i.e., the beam waist proximate the cornea) has a diameter in a range from 200 to 600 um (corresponding to a confocal parameter of about 80 to 700 mm). In other embodiments, the diameter of the first beam waist is in a range 100 to 800. When a first beam waist is smaller than 100 um, due to a tendency of the beam to diverge as a result of diffraction, the beam size on the retina is too large for typical applications; and when a first beam waist is larger than 800 um, the vergency of the beam on the retina causes the confocal length proximate the retina to be too small for typical applications. A beam may be in the visible to infrared wavelengths. Typically, the beam will be in the range 500 nm to 900 nm. In some embodiments, the beam is infrared to avoid a response of the eye.

FIG. 2 illustrates an example of projection apparatus 205 suitable for projecting a beam waist according to aspects of the present invention. The apparatus comprises a laser light source 210 that produces a Gaussian beam 211 having a beam waist 212 that is 1 mm in diameter. A first beam waist 214 of beam 211 is produced by the source.

An optic 220 having a focal length of 300 mm transfers the beam waist to the cornea 201. It will be understood that the beam waist will be transferred by the subject's cornea and lens to form a second beam waist proximate the subject's retina in the manner described above. Optic 220 forms a focal projection apparatus (i.e., the optic converges light). The light in the beam has a vergency that is small enough to maintain a Gaussian beam after the light is transmitted by the optic. Subject positioning apparatus 240 is positioned to hold the subject's cornea such that the beam waist is incident thereon.

Figure 3:
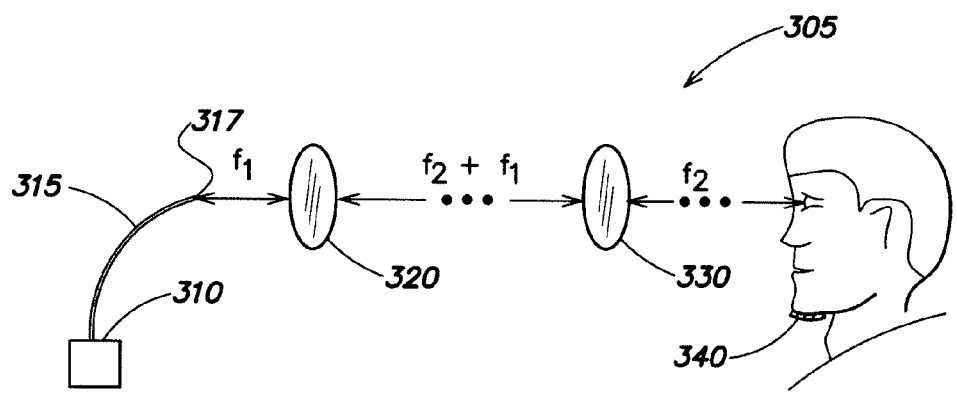
FIG. 3 illustrates another example a suitable projection apparatus.

FIG. 3 illustrates another example a suitable projection apparatus 305. Apparatus 305 comprises an SLD 310 projecting light into a single mode fiber optic 315 having a mode-field diameter of about 5 microns at 800 nm. An emitting end 317 of the fiber optic is located at a front focal point of a lens 320 having a focal length $f_1$ of 5 mm. A second lens 330 having a focal length $f_2$ of 300 mm is located 305 mm from lens 320. Subject positioning apparatus 340 is positioned to hold the subject's cornea 300 mm from the second lens. A Gaussian beam is output from the fiber optic. It will be appreciated that apparatus 300 provides a 300 mm working distance (i.e., the distance between second lens 330 and the front of the subjects' corneas). It will also be appreciated that the discussion above is based on a thin lens assumption, and that one of ordinary skill in the art would be able to account for any thickness(es) of any lens or lenses in the projection apparatus.

It is to be understood that the vergency of the beam after passing through the lens (or lens and pinhole combination) determines whether a Gaussian beam will be generated. Typically, the beam will have a vergency of equal to or less than 5 milliradians (i.e., about 0.3 degrees). In some embodiments, the beam vergency will be greater than 2 milliradians to avoid domination of vergence achieved by the lens by the divergence caused by diffraction (i.e., in a range 2 mR to 5 mR).

It will be appreciated that the wavelength and diameter of a beam at the cornea (or beam vergence at the cornea) are selected such that a second beam waist is projected proximate the retina (i.e., within the confocal region of the beam waist) for eyes having focal powers within a given range. For example, the range of the focal power may include at least a range of −1 to +1 diopters about a nominal diopter value, or may include at least a range of −2 to +2 diopters about a nominal diopter value, or may include at least a range of −3 to +3 diopters about a nominal diopter value, or may include at least a range −6 to +6 diopters about a nominal diopter value, or may include at least a range −12 to +12 diopters about a nominal diopter value, or may include a range −24 to +24 diopters about a nominal diopter value. A typical nominal diopter value is +60 diopters, but any suitable nominal value may be selected.

It will be appreciated that although the illustrated embodiments above show a beam waist 214 projected onto the cornea, according to aspects of the present invention, a portion of the beam within a confocal region around the beam waist may be projected onto the subject's cornea to achieve advantages according to aspects of the present invention. In some embodiments, the portion is located within +/−25% of the confocal parameter from the beam waist. In other embodiments, the portion is within +/−10% of the confocal parameter from the beam waist. It will also be appreciated that projecting a portion of the beam that is closer to a beam waist 114 onto the cornea allows a greater variation in focal power of subject's eyes while still maintaining a small beam spot on the retina.

FIG. 4 is a schematic illustration of an example of an apparatus including a beam projection system as described above with reference to FIG. 1A and optics 300 suitable for use in a Hartmann Schack wavefront aberrometer. Apparatus 400 includes a beam splitter 301 which is arranged to reflect injection beam 113 into eye 200 and to transmit beam 302, after it has been reflected from the subject's retina, to a lenslet array and an image sensor included in optics 300. In some embodiments, the injected beam is injected off-axis as described in U.S. Pat. No. 6,264,328, issued Jul. 24, 2001 to Williams. Said patent includes further details of aberrometers.

Figure 5:
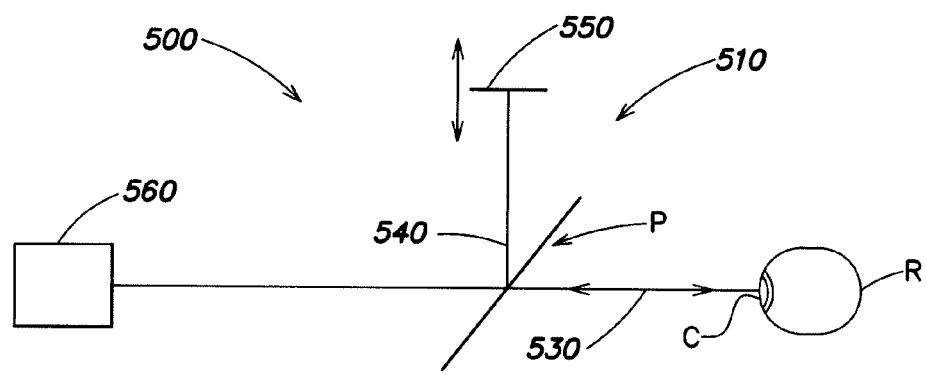
FIG. 5 is a schematic illustration of an example of axial eye length measuring apparatus according to aspects of the present invention.

FIG. 5 is a schematic illustration of an example of an axial eye length measuring apparatus 500 including a beam projection system 560 designed to project a beam as described above with reference to FIG. 1A. The light source in projection system 560 has a short coherence length.

Apparatus 500 includes a Michaelson interferometer 510. In the illustrated example, the Michaelson interferometer includes a test arm 530 and a reference arm 540. The reference arm has a movable mirror 550 suitable for altering the path length of the reference arm. As is understood in the art, the reference arm length can be adjusted to a length $L_1$ so that light from the reference arm forms a first interference pattern (at location P) with light reflected from the cornea C; and the reference arm length can also be adjusted to a length $L_2$ such that light from the reference arm forms a second interference pattern (at location P) with light reflected from the retina R. The length of the eye can thereby be determined by the difference between $L_1$ and $L_2$. It will be appreciated that the quality of the beam reflected from the cornea is better if the size of the beam at the cornea is relatively small; and likewise the quality of the beam reflected from the retina is better if the size of the beam at the retina is relatively small. Accordingly, aspects of the present invention related to establishing a small beam at the retina and at the cornea are advantageous to axial length measurement apparatus.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An ophthalmic apparatus adapted to project a beam of light onto a subject's cornea, comprising:
   a radiation source adapted to generate the light; and
   an optic, the apparatus adapted to position the subject's cornea at a location proximate to a location where the radiation source and the optic project a first waist of a beam of the light, such that a portion of the confocal region of the first waist having a planar wavefront is projected onto the cornea
   wherein the apparatus is configured such that, when the confocal region of the first waist is projected on the cornea, a second beam waist of the beam of light is projected proximate the retina, the retina being within the confocal region of the second beam waist.

2. The apparatus of claim 1, wherein the source is at least partially coherent.

3. The apparatus of claim 1, wherein the source is monochromatic.

4. The apparatus of claim 1, wherein the source comprises a laser.

5. The apparatus of claim 4, wherein the source comprises a laser diode.

6. The apparatus of claim 4, wherein the source provides the light as a Gaussian beam output.

7. The apparatus of claim 1, wherein the source provides the light as a non-Gaussian output.

8. The apparatus of claim 7, further comprising optics adapted to collimate the light to form the beam before the first waist is projected.

9. The apparatus of claim 8, further comprising an aperture to select a size of the beam.

10. The apparatus of claim 1, wherein the optic constitutes a focal optical system.

11. The apparatus of claim 1, wherein the optic constitutes an afocal optical system.

12. The apparatus of claim 1, wherein the source comprises a superluminescent diode.

13. The apparatus of claim 1, wherein the beam has a vergency of 5 milliradians or less.

14. The apparatus of claim 1, wherein the beam has a vergency of greater than 2 milliradians and less than 5 milliradians.

15. The apparatus of claim 1, wherein the apparatus comprises a wavefront aberrometer.

16. The apparatus of claim 1, wherein the apparatus comprises an axial eye length measuring apparatus.

17. The apparatus of claim 1, wherein the apparatus comprises a refractometer.

18. The apparatus of claim 1, wherein the apparatus is adapted to position the subject's cornea at the location where the radiation source and the optic project the first waist.

19. The apparatus of claim 1, wherein the first waist has a diameter of 200 to 600 um.

20. The apparatus of claim 1, wherein the first waist has a diameter of 100 to 800 um.

21. The apparatus of claim 1, wherein the apparatus is configured such that for eyes having focal powers within at least a range of −1 to +1 diopters the retina is within the confocal region of the second beam waist.

22. A method of illuminating a subject's eye, comprising:
projecting a first beam waist of a beam of light such that a portion of the confocal region of the first beam waist has a planar wavefront projected onto the subject's cornea and such that a second beam waist is projected proximate the subject's retina while the first beam waist is projected on the cornea, the retina being within the confocal region of the second beam waist.

23. The method of claim 22, wherein the light is monochromatic.

24. The method of claim 22, further comprising a step of generating the beam from an output of a laser.

25. The method of claim 22, further comprising a step of generating the beam from an output of a laser diode.

26. The method of claim 24, wherein the beam is a Gaussian beam output of the laser.

27. The method of claim 22, further comprising a step of generating a non-Gaussian output of the light, prior to the step of projecting.

28. The method of claim 27, further comprising a step of collimating the non-Gaussian output to form the beam, prior to the step of projecting.

29. The method of claim 22, further comprising a step of selecting a size of the beam using an aperture, prior to the step of projecting.

30. The apparatus of claim 22, wherein the beam has a vergency of 5 milliradians or less.

* * * * *